(12) United States Patent
Yoo et al.

(10) Patent No.: US 11,612,339 B2
(45) Date of Patent: Mar. 28, 2023

(54) BIOMETRIC SENSOR

(71) Applicant: KOREA ADVANCED INSTITUTE OF SCIENCE AND TECHNOLOGY, Daejeon (KR)

(72) Inventors: Seunghyup Yoo, Daejeon (KR); Hyeonwoo Lee, Goyang-si (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 172 days.

(21) Appl. No.: 17/119,814

(22) Filed: Dec. 11, 2020

(65) Prior Publication Data

US 2021/0177320 A1 Jun. 17, 2021

(30) Foreign Application Priority Data

Dec. 12, 2019 (KR) .......................... 10-2019-0165306

(51) Int. Cl.
*A61B 5/1455* (2006.01)
*H01L 27/28* (2006.01)
(Continued)

(52) U.S. Cl.
CPC ........ *A61B 5/14552* (2013.01); *A61B 5/0205* (2013.01); *A61B 5/02007* (2013.01);
(Continued)

(58) Field of Classification Search
CPC ............ A61B 5/14552; A61B 5/02007; A61B 5/0205; A61B 5/0261; A61B 5/0295;
(Continued)

(56) References Cited

U.S. PATENT DOCUMENTS

2002/0035315 A1\* 3/2002 Ali .......................... A61B 5/746
600/323
2007/0123756 A1\* 5/2007 Kitajima ............ A61B 5/14552
600/595
(Continued)

FOREIGN PATENT DOCUMENTS

JP 2013-000157 A 1/2013
JP 2013000157 A \* 1/2013
(Continued)

OTHER PUBLICATIONS

KR Office Action in Application No. 10-2019-0165306 dated Jun. 29, 2021.

*Primary Examiner* — Eric F Winakur
*Assistant Examiner* — Abid A Mustansir
(74) *Attorney, Agent, or Firm* — Maschoff Brennan

(57) ABSTRACT

According to one embodiment of the present disclosure, a biometric sensor includes a flexible substrate, a first light-emitting part disposed on one side of the flexible substrate to output first light toward the body, a second light-emitting part disposed on one side of the flexible substrate to output second light different from the first light toward the body, an elastomer disposed on one side of the flexible substrate in a shape surrounding the first light-emitting part and the second light-emitting part, and a light-receiving part disposed on the other side of the flexible substrate to receive third light corresponding to the first light and fourth light corresponding to the second light.

18 Claims, 8 Drawing Sheets

(51) Int. Cl.
  *H01L 33/62*    (2010.01)
  *H01L 51/00*    (2006.01)
  *H01L 51/42*    (2006.01)
  *H01L 51/44*    (2006.01)
  *A61B 5/0295*   (2006.01)
  *A61B 5/0205*   (2006.01)
  *A61B 5/02*     (2006.01)
  *A61B 5/026*    (2006.01)
  *A61B 5/024*    (2006.01)

(52) U.S. Cl.
  CPC .......... *A61B 5/0261* (2013.01); *A61B 5/0295* (2013.01); *H01L 27/286* (2013.01); *H01L 33/62* (2013.01); *H01L 51/0097* (2013.01); *H01L 51/4253* (2013.01); *H01L 51/448* (2013.01); *A61B 5/02433* (2013.01); *A61B 2562/0238* (2013.01); *A61B 2562/164* (2013.01); *A61B 2562/166* (2013.01)

(58) Field of Classification Search
  CPC ........ A61B 5/02433; A61B 2562/0238; A61B 2562/164; A61B 2562/166; A61B 5/02416; A61B 5/14551; A61B 5/0059; A61B 5/683; A61B 2562/18; H01L 27/286; H01L 33/62; H01L 51/0097; H01L 51/4253; H01L 51/448; H01L 27/3227; H01L 27/3204; H01L 25/167; Y02E 10/549
  See application file for complete search history.

(56) References Cited

U.S. PATENT DOCUMENTS

| | | | |
|---|---|---|---|
| 2010/0331640 | A1* | 12/2010 | Medina .............. A61B 5/14535 600/324 |
| 2016/0198962 | A1* | 7/2016 | Park ..................... A61B 5/0295 600/480 |
| 2019/0313954 | A1 | 10/2019 | Yoo et al. |
| 2019/0320950 | A1* | 10/2019 | Yoda .................... A61B 5/6826 |
| 2020/0128670 | A1* | 4/2020 | Chong Rodriguez ....................... H05K 1/0209 |

FOREIGN PATENT DOCUMENTS

| | | |
|---|---|---|
| KR | 10-2016-0086710 A | 7/2016 |
| KR | 10-2019-0095715 A | 8/2019 |
| KR | 10-2019-0114386 A | 10/2019 |

* cited by examiner

BIOMETRIC SENSOR

CROSS-REFERENCE TO RELATED APPLICATION

This application claims priority to and the benefit of Korean Patent Application No. 10-2019-0165306, filed on Dec. 12, 2019, the disclosure of which is incorporated herein by reference in its entirety.

BACKGROUND

1. Field of the Invention

The present disclosure relates to a biometric sensor, and more particularly, to a biometric sensor capable of measuring a heart rate and blood oxygen saturation by mounting a light-receiving part composed of an organic photodiode therein.

2. Discussion of Related Art

Generally, in a medical institution or general household, biometric sensors are used to identify blood vessel information (e.g., a heart rate signal, photoplethysmogram, oxygen saturation, photoplethysmography (PPG), or the like), respiration information, other biological activities, or the like. In particular, a heart rate and oxygen saturation sensor capable of measuring blood oxygen saturation using light absorption of hemoglobin has been used. The heart rate and oxygen saturation sensors using optical elements may relatively simply confirm biometric information in a noninvasive manner, and thus are in high demand.

A conventional driving method of a conventional heart rate and oxygen saturation sensor using an optical element may be largely divided into a transmission method and a reflection method.

The transmission method uses a light-emitting diode (LED) and a photodiode (PD), and a biological medium (e.g., a finger, an ear lobe, or the like) is located between the LED and the PD. In this case, the transmission method is a method of acquiring information on changes in blood vessels inside the biological medium by reception of light, which is emitted (or irradiated) from the LED and transmitted through the biological medium, by the PD.

In the reflection method, an LED is located to be coplanar with a PD, and the reflection method is a method of acquiring information on changes in blood vessels inside the biological medium by reception of light, which is emitted from the LED and reflected by an inside of the biological medium, by the PD.

Light irradiated to the biological medium is scattered inside the skin and thus distributed more widely than an incident angle of the light irradiated to the biological medium. In addition, degrees of absorption and scattering in the biological medium vary according to a wavelength of light emitted from an LED, so that the light distribution tends to vary.

Conventional transmission and reflection type heart rate and oxygen saturation sensors are generally configured by arranging optical elements based on silicon or group III-V compound semiconductors. The conventional inorganic semiconductor-based optical element has difficulty in securing mechanical flexibility and stretchability, and thus is limited in application to various parts of the human body. Further, a spatial arrangement of light-emitting elements and light-receiving elements should be optimized to efficiently receive light, but the conventional inorganic semiconductor-based optical element is mainly implemented in a rectangular shape, and thus is very limited in design freedom for obtaining high-efficiency signals.

A wearable health care sensor that is preferable for constant monitoring requires small power consumption of a light source for securing a sufficient amount of signal, but the limit of design freedom of present technologies may be a serious problem in reduction of the power consumption.

Further, there are many cases in which high brightness is required for a heart rate and oxygen saturation sensor using light, and in the high brightness, external quantum efficiency (EQE) is less efficient in an organic LED (OLED) than in an LED. The conventional heart rate and oxygen saturation sensor uses an OLED and thus has a problem in that EQE is low as compared to the case of using an LED, so that an improvement of the EQE is needed.

SUMMARY OF THE INVENTION

The present disclosure is directed to providing a biometric sensor having a structure in which light-receiving efficiency is remarkably increased.

The present disclosure is also directed to providing a biometric sensor capable of being driven with low power by optimally receiving light through the above structure.

The present disclosure is also directed to providing a biometric sensor capable of being driven with high external quantum efficiency at high brightness.

It is to be understood that the object of the present disclosure is not limited to the above-described objects and can be expanded in various ways without departing from the spirit and scope of the present disclosure.

According to an aspect of the present disclosure, there is provided a biometric sensor including a flexible substrate, a first light-emitting part disposed on one side of the flexible substrate to output first light toward the body, a second light-emitting part disposed on one side of the flexible substrate to output second light different from the first light toward the body, an elastomer disposed on one side of the flexible substrate in a shape surrounding the first light-emitting part and the second light-emitting part, and a light-receiving part disposed on the other side of the flexible substrate to receive third light corresponding to the first light and fourth light corresponding to the second light, wherein the third light is light obtained by reflection of the first light by the body, the fourth light is light obtained by reflection of the second light by the body, the elastomer includes a first region disposed between the first light-emitting part and the second light-emitting part, and the first region is a path through which the third light and the fourth light reflected by the body are transmitted.

BRIEF DESCRIPTION OF THE DRAWINGS

The above and other objects, features, and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
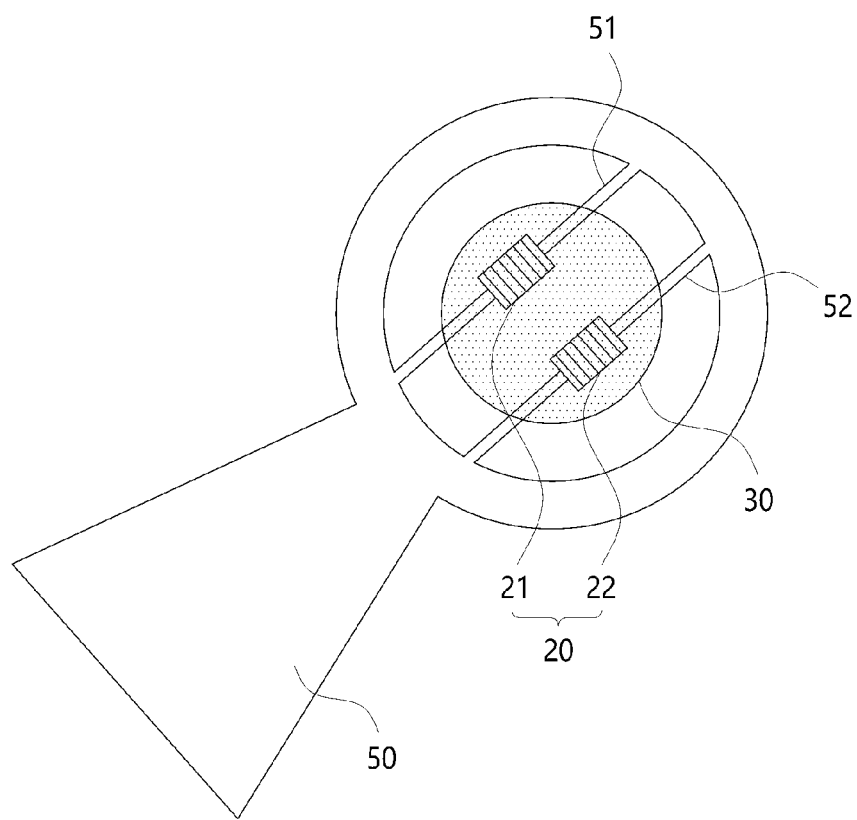
FIG. 1 is a schematic perspective view of a biometric sensor according to one embodiment of the present application.

Hereinafter, embodiments of the present disclosure will be described in detail with reference to the accompanying drawings. Detailed descriptions of constituent elements of the present disclosure that can be clearly grasped and easily reproduced by a person skilled in the art will be omitted to avoid making the subject matter of the present disclosure unclear.

According to one embodiment of a biometric sensor disclosed in the present application, a wavelength of first light output from a first light-emitting part may be different from a wavelength of second light output from a second light-emitting part.

According to one embodiment of the biometric sensor disclosed in the present application, the first light output from the first light-emitting part may be output for a first period, the second light output from the second light-emitting part may be output for a second period, the first light and the second light may be alternately output, and a controller may detect first information on the basis of the first light incident on the light-receiving part for the first period and detect second information on the basis of the second light incident on the light-receiving part for the second period.

According to one embodiment of the biometric sensor disclosed in the present application, the light-receiving part is formed in a shape surrounding an upper surface of each of the first light-emitting part and the second light-receiving part, and at least a partial surface of the light-receiving part corresponding to a direction perpendicular to the upper surface of at least one of the first light-emitting part and the second light-emitting part may overlap the upper surface of at least one of the first light-emitting part and the second light-emitting part.

According to one embodiment of the biometric sensor disclosed in the present application, the light-receiving part may include a first light-receiving part and a second light-receiving part, third light reflected by the body may be received by at least one of the first light-receiving part and the second light-receiving part, and fourth light reflected by the body may be received by at least one of the first light-receiving part and the second light-receiving part.

According to one embodiment of the biometric sensor disclosed in the present application, the first light may be output from the first light-emitting part toward the body located in a region in a direction opposite to a direction in which a flexible substrate is located, and the second light may be output from the second light-emitting part toward the body located in a region in the direction opposite to the direction in which the flexible substrate is located.

According to one embodiment of the biometric sensor disclosed in the present application, the first light-emitting part may a red light-emitting diode (red LED), and the second light-emitting part may be a near infrared (NIR) LED.

According to one embodiment of the biometric sensor disclosed in the present application, the flexible substrate may be made of polyethylene terephthalate (PET) through which the third light and the fourth light are transmitted.

According to one embodiment of the biometric sensor disclosed in the present application, an elastomer may be made of polydimethylsiloxane (PDMS), silicone, or a combination thereof through which the third light and the fourth light are transmitted.

According to one embodiment of the biometric sensor disclosed in the present application, the biometric sensor may further include at least one or more protective layers configured to block external moisture and/or oxygen.

According to one embodiment of the biometric sensor disclosed in the present application, the elastomer may include a second region and a third region, wherein the second region may be located at a side surface opposite to one side surface of the first light-emitting part, which is connected to the first region, the third region may be located at a side surface opposite to one side surface of the second light-emitting part, which is connected to the first region, the second region or the third region may be a path through which the third light and the fourth light reflected by the body are transmitted, a transmitted amount of the third light corresponding to the first light emitted from the first light-emitting part may be greater in the first region than in the third region, and a transmitted amount of the fourth light corresponding to the second light emitted from the second light-emitting part may be greater in the first region than in the second region.

According to one embodiment of the biometric sensor disclosed in the present application, the flexible substrate may include a fourth region including a first dead zone in contact with the first light-emitting part, a fifth region including a second dead zone in contact with the second light-emitting part, and a sixth region disposed between the fourth region and the fifth region, wherein the sixth region may be a path through which the third light and the fourth light reflected by the body are transmitted, and in the first dead zone and the second dead zone, the third light and the fourth light may not be transmitted.

According to one embodiment of the biometric sensor disclosed in the present application, the biometric sensor may further include a flexible printed circuit board (FPCB) located at the other side of the flexible substrate, wherein wires connected from an external power source may be mounted in the FPCB.

According to one embodiment of the biometric sensor disclosed in the present application, the controller may sense a change in blood vessels, blood flow, a heart rate, oxygen saturation, photoplethysmogram, photoplethysmography (PPG), or a combination thereof on the basis of the first information and the second information.

According to one embodiment of the biometric sensor disclosed in the present application, a size of the elastomer may be set such that both the third light and the fourth light incident on the light-receiving part are transmitted through the elastomer. According to one embodiment of the biometric sensor disclosed in the present application, the flexible substrate may further include a seventh region and an eighth region, wherein the seventh region may be located on a side opposite to one side of the fourth region, which is connected to one side of the sixth region, the eighth region may be located on a side opposite to one side of the fifth region, which is connected to the other side of the sixth region, a transmitted amount of the third light corresponding to the first light emitted from the first light-emitting part may be greater in the sixth region than in the eighth region, and a transmitted amount of the fourth light corresponding to the second light emitted from the second light-emitting part may be greater in the sixth region than in the seventh region.

According to one embodiment of the biometric sensor disclosed in the present application, the first light-emitting part and the second light-emitting part may be connected to the wires mounted in the FPCB, and the wires may be configured to be surrounded by the elastomer or to be disposed between the flexible substrate and the elastomer.

According to one embodiment of the biometric sensor disclosed in the present application, the wires may include a first wire and a second wire, the first wire may be connected to the first light-emitting part, and the second wire may be connected to the second light-emitting part.

Hereinafter, a biometric sensor according the present disclosure will be described.

Figure 2:
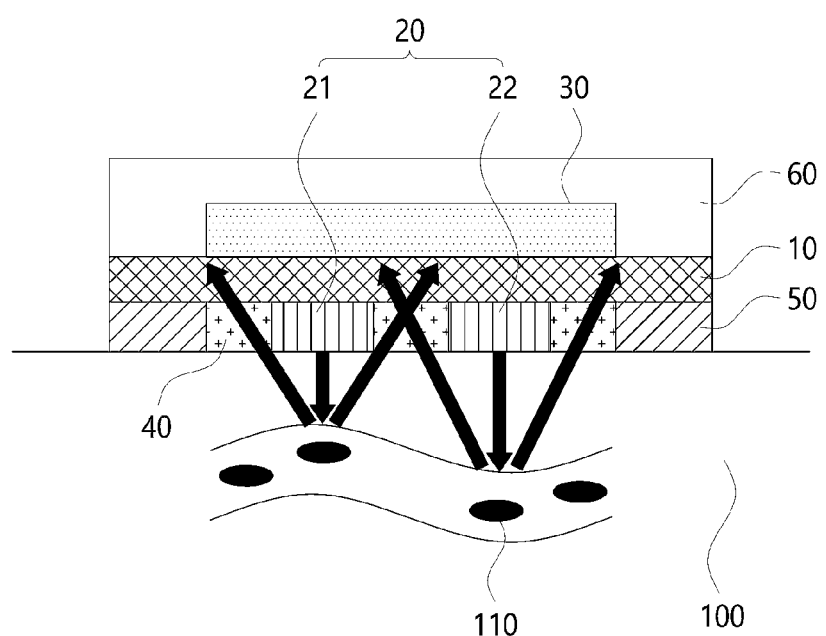
FIG. 2 is a cross-sectional view illustrating an operating principle and a configuration of the biometric sensor according to one embodiment of the present application.
Figure 3:
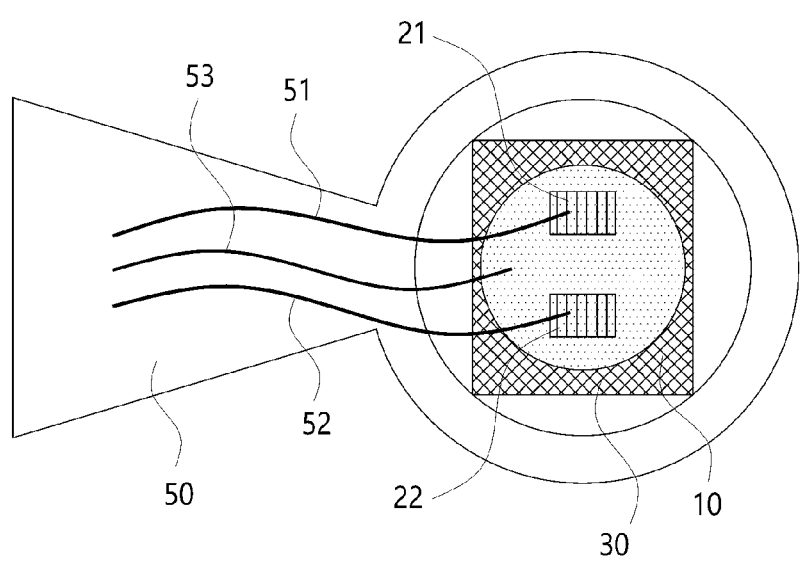
FIG. 3 is a plan view of the biometric sensor according to one embodiment of the present application.

Reference is made to FIGS. 1 to 3. FIG. 1 is a schematic perspective view of a biometric sensor according to one embodiment of the present application. FIG. 2 is a cross-sectional view illustrating an operating principle and a configuration of the biometric sensor according to one embodiment of the present application. FIG. 3 is a plan view of the biometric sensor according to one embodiment of the present application.

The biometric sensor according to one embodiment of the present disclosure may include a flexible substrate 10, a light-receiving part 30, a light-emitting part 20, an elastomer 40, an FPCB 50, and a protective layer 60.

According to one embodiment of the present disclosure, the biometric sensor may include the flexible substrate 10. The flexible substrate 10 may serve to fix or support the light-receiving part 30, the light-emitting part 20, the elastomer 40, and the like to be described later. In addition, the flexible substrate 10 may be configured such that the overall shape of the biometric sensor may be flexibly deformed according to the shape of a body 100. In other words, since the flexible substrate 10 serves to maintain the shape of the biometric sensor and support components and also serves to allow the shape of the biometric sensor to be flexibly deformed according to a part of the body 100, with which the biometric sensor is brought into contact for sensing, the flexible substrate 10 may have physical properties having a certain degree of durability and flexibility.

Various components for sensing biometric information may be disposed on the flexible substrate 10. For example, like a general circuit board, electrical wires connecting various components (circuit components or the like) based on a circuit design may be represented by a wiring diagram and may be reproduced on the flexible substrate using electrical conductors on an insulating material.

Further, the flexible substrate 10 may include components such as electrical components and include wires formed therein that electrically connect the components, and may perform a function of mechanically fixing the components in addition to a function of electrically connecting the components.

Referring to FIG. 2, according to one embodiment of the present disclosure, the light-receiving part 30, the light-emitting part 20, the elastomer 40, and the FPCB 50 may be located on the flexible substrate to be connected to the flexible substrate.

For example, the light-receiving part 30 to be described below may be located on one side of the flexible substrate 10. In addition, the FPCB 50, which will be described below, on which one or more light-emitting parts 20, the elastomer 40, and wires 51, 52, and 53 configured to supply power to the light-emitting parts 20 and the light-receiving part 30 are mounted may be located on the other side of the flexible substrate 10.

As described above, since the components for sensing biometric information may be located on the flexible substrate 10, the flexible substrate 10 may be made of any suitable material capable of maintaining the overall shape of the biometric sensor by having a certain degree of durability capable of supporting and/or fixing the components.

Further, the flexible substrate 10 may have a flexible characteristic so that the shape thereof may be changed according to a body part. In other words, the flexible substrate 10 may have a flexible characteristic so that the flexible substrate 10 may be bent while having a partially curved surface so as to correspond to the shape of a curvature of the body. For example, when the biometric sensor according to one embodiment of the present disclosure is used to sense biometric information of a wrist, the biometric sensor may be bent to have a curvature so as to correspond to a curvature of the wrist. Since the wrist has a partially straight shape and partly curved shape with a curvature, the biometric sensor should also have a flexible characteristic to implement the partially curved shape. To this end, the flexible substrate 10 may be made of a material capable of realizing a certain degree of flexibility.

In summary, the flexible substrate 10 may be made of a material that allows the biometric sensor to have at least a certain degree of durability and flexibility.

Further, according to one embodiment of the present disclosure, light emitted from the light-emitting part 20 is reflected by an inside of a biological medium and is received by the light-receiving part 30 through the flexible substrate 10, so that the flexible substrate may be made of a material that minimizes the loss of the reflected light.

For example, the flexible substrate may be transparent so that the flexible substrate transmits the reflected light.

Further, the light-emitting part includes a first light-emitting part and a second light-emitting part, the first light-emitting part may be configured as a red LED, and the second light-emitting part may be configured as an NIR LED, and light emitted from the red LED and the NIR LED has a relatively high transmittance, and thus the flexible substrate according to the present disclosure may be a flexible substrate capable of transmitting the light emitted from the red LED and the NIR LED even though the transmittance is relatively low.

According to one exemplary embodiment of the present disclosure, the flexible substrate may be made of a synthetic resin such as polyethylene terephthalate (PET) or the like. However, the present disclosure is not limited to PET, and the flexible substrate may be made of a material having a certain degree of durability and a flexible characteristic.

The biometric sensor according to one embodiment of the present disclosure may include the light-emitting part 20. The light-emitting part 20 may be located on one side of the flexible substrate.

The light-emitting part 20 may emit (irradiate or output) light. That is, various components capable of emitting light may be used as the light-emitting part 20. For example, the light-emitting part 20 may be configured as an LED, an IR LED, an NIR LED, a laser diode, an organic LED (OLED), or an appropriate combination thereof.

However, when the biometric sensor is used for a heart rate and oxygen saturation sensor requiring high brightness, the component of the light-emitting part 20 may be an LED-based component such as an LED or an NIR LED. External quantum efficiency (EQE) of the LED-based component is high at high brightness as compared to that of the OLED-based component, and thus when the biometric sensor according to the present disclosure is used for the heart rate and oxygen saturation sensor, the EQE is increased by configuring the light-emitting part 20 as an LED-based component such as an LED or an NIR LED, thereby reducing power consumption.

In the biometric sensor according to one embodiment of the present disclosure, at least one or more light-emitting parts 20 may be provided. For example, the light-emitting part 20 may include a first light-emitting part 21 and a second light-emitting part 22, and each of the first light-emitting part 21 and the second light-emitting part 22 may be configured as an LED, an NIR LED, an IR LED, a laser diode, an OLED, or a combination thereof.

According to one embodiment of the present disclosure, light emitted from the first and second light-emitting parts 21 and 22 may have the same wavelength, but may have different wavelengths. In this case, the light emitted from the first and second light-emitting parts 21 and 22 may be output at a wavelength determined to be advantageous on the basis of the location and type of body to be sensed, the degree of absorption by the body, or the like.

For example, the first and second light-emitting parts 21 and 22 may both be configured as an LED, but may be configured to emit light with different wavelengths. Alternatively, the first light-emitting part 21 may be configured as an LED that emits light other than NIR, while the second light-emitting part 22 may be configured an NIR LED to emit light with a different wavelength.

In the biometric sensor according to one embodiment of the present disclosure, the first light-emitting part 21 may be configured as a red LED, and the second light-emitting part 22 may be configured as an NIR LED.

In the case of a conventional biometric sensor, when a first light-emitting part and a second light-emitting part are respectively configured as a red LED and an NIR LED, due to the characteristics of the LEDs emitting light having a relatively long wavelength and penetrating deeply, the biometric sensor with a transmission method is manufactured.

However, the biometric sensor according to one embodiment of the present disclosure may be configured to measure oxygen saturation using a reflection method when the first light-emitting part and the second light-emitting part are respectively configured as a red LED and an NIR LED. In addition, the biometric sensor according to one embodiment of the present disclosure has an effect of having a higher power efficiency than the conventional biometric sensor with a transmission method, as well as the fact that the biometric sensor may be configured to measure oxygen saturation using a reflection method.

Referring to FIG. 2, according to one embodiment of the present disclosure, the light-emitting part 20 including the first and second light-emitting parts 21 and 22 may be located on one side of the flexible substrate 10. The first and second light-emitting parts 21 and 22 may be located side by side on one side of the flexible substrate 10 by being in contact with each other, but the first and second light-emitting parts 21 and 22 may be located at a predetermined interval on one side of the flexible substrate 10.

Further, the elastomer 40, which will be described below, located on one side of the flexible substrate 10 may be located at the periphery of each of the first and second light-emitting parts 21 and 22. For example, the elastomer 40 may be disposed between the first and second light-emitting parts 21 and 22. In addition, the elastomer 40 may be disposed between the FPCB 50 located on one side of the flexible substrate 10 and each of the first and second light-emitting parts 21 and 22.

Preferably, the elastomer 40 may be made of a material capable of transmitting light. With such a configuration, light emitted from each of the first and second light-emitting parts 21 and 22 is reflected by an object inside a body to be reflected light, and may be received by the light-receiving part 30 through the elastomer 40, so that efficient light reception may be achieved.

This will be described in detail below.

According to one embodiment of the present disclosure, the first light-emitting part 21 may receive power from a device including the biometric sensor through a first wire 51 embedded in the FPCB 50 to be described below. The first light-emitting part 21 may convert the received power into light energy to emit first light of a specific wavelength.

Similarly, the second light-emitting part 22 may receive power from the device including the biometric sensor through a second wire 52 embedded in the FPCB 50 to be described below. The second light-emitting part 22 may convert the received power into light energy to emit second light of a specific wavelength.

In addition, the light-emitting part 20 including the first and second light-emitting parts 21 and 22 may be shielded by the protective layer to block oxygen and moisture originating from the outside or from the body.

The biometric sensor according to one embodiment of the present disclosure may include the light-receiving part 30. The light-receiving part 30 may be located on the flexible substrate 10. In particular, although the light-receiving part 30 may be located on the same side as one side of the flexible substrate on which the light-emitting part 20 is located, according to the exemplary embodiment of the present disclosure, the light-receiving part 30 may be located on a side (or the other side of the flexible substrate) opposite to one side of the flexible substrate on which the light-emitting part 20 is located. Since the light-receiving part 30 is located on the side opposite to the side on which the light-emitting part 20 is located with respect to the flexible substrate 10, a shape in which the light-receiving part 30 surrounds the light-emitting part 20 may be obtained, so that a low-power-based biometric sensor that increases light reception efficiency may be implemented. Hereinafter, technical features of the light-receiving part will be described in detail.

According to one embodiment of the present disclosure, the biometric sensor may include the light-receiving part 30. The light-receiving part 30 may be configured as an appropriate element capable of receiving light such as a photodiode (PD), but according to the exemplary embodiment of the present disclosure, the light-receiving part 30 may be configured as an organic photodiode (OPD).

An existing silicon-based optical element has a structure that makes it difficult for a light-receiving part to receive light efficiently. This is because that a biometric sensor manufactured using a silicon-based PD or the like is inflexible and invariable to change in shape, and thus is difficult to be implemented in a form capable of efficiently receiving light.

However, patterns may be freely formed in an OPD, which is manufactured using an organic semiconductor manufacturing process in which pattern formation is relatively free, and thus there is an advantage of being able to manufacture the structure of the light-receiving part into a target structure. In addition, the OPD is more flexible than the existing silicon-based optical element, and thus there is an advantage of being able to implement a partial curved surface.

In the biometric sensor according to one embodiment of the present disclosure, the light-receiving part 30 may be configured as an OPD. A structure surrounding the light-emitting part 20 in all directions may be implemented using an OPD in which patterns are freely formed. Specifically, it is difficult to predict a reflection path of the light reflected by the object inside the body due to scattering, but by forming the light-receiving part 30 in a structure surrounding the light-emitting part 20, the possibility of a loss of the reflected light is lowered, so that the reflected light reception efficiency of the light-receiving part 30 may be increased.

According to one embodiment of the present disclosure, the light-receiving part 30 may be formed in a structure surrounding the light-emitting part 20. In this case, when a plurality of light-emitting parts 20 are formed, the light-receiving part 30 may be formed so as to surround all of the plurality of light-emitting parts. For example, in the case in which the light-emitting part 20 includes the first light-emitting part 21 and the second light-emitting part 22, the light-receiving part 30 may be formed to surround both the first light-emitting part 21 and the second light-emitting part 22. As shown in FIG. 3, the light-receiving part 30 is formed in a shape surrounding or covering upper surfaces of the first and second light-emitting parts 21 and 22, and at least a partial surface of the light-receiving part 30 corresponding to a direction perpendicular to the upper surface of at least one of the first and second light-emitting parts 21 and 22 overlaps the upper surface of at least one of the first and second light-emitting parts 21 and 22. In other words, when the biometric sensor according to one embodiment of the present disclosure is observed in a top view, the light-receiving part 30 may be configured such that a partial surface of the light-receiving part 30 overlaps the upper surface of the first light-emitting part 21 or the upper surface of the second light-emitting part 22. When the first and second light-emitting parts 21 and 22 are viewed from above the light-receiving part 30, the light-receiving part 30 may cover all regions of the first and second light-emitting parts 21 and 22. The outermost side of the first and second light-emitting parts 21 and 22 may be located in a direction toward the center of the light-receiving part 30 than the edge of the light-receiving part 30. In addition, the sum of areas occupied by the first and second light-emitting parts 21 and 22 may be less than an area of the light-receiving part 30.

Alternatively, in the case in which the plurality of light-emitting parts 20 are formed, the light-receiving part may also be implemented as a first light-receiving part and a second light-receiving part respectively surrounding the first light-emitting part and the second light-emitting part. In this case, the first light-receiving part and the second light-receiving part may be configured such that light, which is output from the first light-emitting part and reflected by the inside of the body, is received by at least one of the first light-receiving part and the second light-receiving part. In addition, the first light-receiving part and the second light-receiving part may be configured such that light, which is output from the second light-emitting part and reflected by the inside of the body, is received by at least one of the first light-receiving part and the second light-receiving part. In addition, the first light-receiving part and the second light-receiving part may be configured to be connected to each other.

Further, the light-receiving part may be configured to include a corresponding number of light-receiving parts to receive reflected light originating from each of the plurality of light-emitting parts. For example, it may be configured such that the reflected light originating from the first light-emitting part is received by the first light-receiving part, and the reflected light originating from the second light-emitting part is received by the second light-receiving part.

In the biometric sensor according to one embodiment of the present disclosure, the light-receiving part 30 may be located above the light-emitting parts 20 based on the body 100 so that the light-receiving part 30 surrounds the light-emitting parts 20. For example, when the light-emitting parts 20 are located on one side of the flexible substrate 10, the light-receiving part 30 may be located on the other side of the flexible substrate 10. In this case, such a structure may be implemented by stacking the light-emitting parts 20 on one side of the flexible substrate 10 and stacking the light-receiving part 30 on the other side of the flexible substrate 10.

The biometric sensor according to one embodiment of the present disclosure includes the light-receiving part, and in particular, the light-receiving part may be configured as an OPD. The light-receiving part may be configured to receive light reflected by the inside of the body, generate a current on the basis of the received light, and observe a change in voltage of the light-receiving part through an external receiving circuit. In particular, the light-receiving part composed of an OPD may receive information on each of reflected light for a part of the body, which is not moving inside the body, and reflected light whose light absorption level changes according to the movement of blood vessels, and it may be configured such that current, which is converted in the light-receiving part according to the light absorption level of the received reflected light, is output as an alternating current (AC) or direct current (DC) value.

Further, the biometric sensor according to one embodiment of the present disclosure may be configured such that an upper surface and a side surface portion of the light-receiving part are surrounded by the protective layer so as to block moisture and/or oxygen from the outside.

Referring to FIG. 2, in the biometric sensor according to one embodiment of the present disclosure, the light-emitting part 20 and the light-receiving part 30 are located in the same direction based on the body. This is due to a reflection method in which light emitted from the light-emitting part 20 is irradiated toward the body 100 and the light reflected by an object 110 inside the body is received by the light-receiving part 30.

Here, the light-receiving part 30 of the biometric sensor according to one embodiment of the present disclosure may be configured to be located above the light-emitting part 20 based on the body 100.

Accordingly, in the light-emitting part 20 including the first and second light-emitting parts 21 and 22, when light emitted toward the body 100 is partially reflected by the object 110 inside the body, in order for the light-receiving part 30 to receive the reflected light, an element made of a material capable of transmitting the reflected light needs to be located on the periphery of the light-emitting part 20.

According to one embodiment of the present disclosure, the biometric sensor may further include the elastomer 40 located on the periphery of the first and second light-emitting parts 21 and 22.

The periphery of the first and second light-emitting parts 21 and 22 may refer to a region between the first and second light-emitting parts 21 and 22 and/or a region between the FPCB 50 to be described below and each of first and second light-emitting parts 21 and 22.

In other words, the elastomer 40 may be disposed in a region between the first and second light-emitting parts 21 and 22. In addition, the elastomer 40 may be located in a region between the first light-emitting part 21 and the FPCB 50. In addition, the elastomer 40 may be located in a region between the second light-emitting part 22 and the FPCB 50.

According to one embodiment of the present disclosure, the elastomer 40 may be made of a material capable of transmitting the light reflected by the object 110 inside the body 100. Specifically, the elastomer 40 may be made of a material having a transparent characteristic capable of transmitting the reflected light. For example, the elastomer 40 may be a material such as polydimethylsiloxane (PDMS), Silbione, or silicone. Since the biometric sensor includes the elastomer 40 capable of transmitting light as described above, a ratio of the reflected light that is not received by the light-receiving part 30 on the upper side may be reduced, so that the biometric sensor may have an advantage of increasing light reception efficiency.

Further, since it is configured such that reflected light originating from each of the first and second light-emitting parts 21 and 22 is transmitted through the elastomer 40 to be received by the light-receiving part 30, the size of the elastomer 40 may be an important factor in receiving the reflected light. In this case, the size of the elastomer 40 may be determined so that both reflected light originating from the first light-emitting part and reflected light originating from the second light-emitting part, which are incident on the light-receiving part, are transmitted through the elastomer.

For example, the size of the elastomer 40 may be determined in consideration of an outermost optical angle of the reflected light originating from each of the first and second light-emitting parts 21 and 22, which is incident on the light-receiving part 30 and an outer diameter of the light-receiving part.

According to one embodiment of the present disclosure, the biometric sensor may be in contact with the body 100 (e.g., skin) to sense specific information in the body. Referring to FIG. 2, the biometric sensor may include the elastomer 40, and the elastomer 40 may be in contact with the body. Thus, the elastomer 40 may be made of a material that is compatible with the body. That is, since the elastomer may be in contact with the body, a material harmless to the body may be selected as the material of the elastomer.

In addition, when the biometric information is sensed, an error may be generated in the biometric information measurement due to the movement of a biometric sensor device, and thus the biometric sensor device may be required to be in close contact with the body 100 (e.g., skin). To this end, the elastomer 40, which may be in contact with the body, may be made of a material having adhesiveness. In other words, the material of the elastomer 40 may be selected from materials having adhesiveness to reduce the movement of the biometric sensor when the biometric sensor is used by being brought into close contact with the body.

In addition, the elastomer may be used to maintain the overall structure of the biometric sensor. For example, the elastomer may be located in a region between the light-emitting parts or a region between the light-emitting part and the FPCB in order to support the light-emitting part disposed on one side of the flexible substrate or a component such as the FPCB. In the absence of the elastomer, a load is applied to the flexible substrate in a portion in which the components such as the light-emitting part are located, so that the overall structure of the biometric sensor is not maintained, thereby causing errors or distortions in information sensing by the biometric sensor. The biometric sensor disclosed in the present application includes the elastomer, and thus may increase the accuracy of sensing biometric information by maintaining the structure of the biometric sensor to be constant.

Referring to FIGS. 1 to 3, the biometric sensor according to one embodiment of the present disclosure may include the FPCB 50.

The FPCB 50 may be located on the flexible substrate 10. The FPCB 50 may be located on one side of the flexible substrate 10. The FPCB 50 may be located on one side of the flexible substrate 10 on which the first and second light-emitting parts 21 and 22 are located.

The FPCB 50 may have a height corresponding to a height of each of the first and second light-emitting parts 21 and 22. Further, the FPCB 50 may have a height corresponding to that of the elastomer 40. Since the FPCB 50 has the height corresponding to that of each of the first and second light-emitting parts 21 and 22 and the elastomer 40, all the components of the biometric sensor may be manufactured without a step difference.

Since all the components of the biometric sensor may be manufactured without a step difference, a separation between the body to be measured and the biometric sensor may be prevented for each region, thereby improving measurement accuracy.

Like a general circuit board, electrical wires connecting various components (circuit components or the like) based on a circuit design may be represented by a wiring diagram and may be reproduced on the FPCB using electrical conductors on an insulating material.

Further, the FPCB may include components such as electrical components and include wires formed therein that electrically connect the components, and may perform a function of mechanically fixing the components in addition to a function of electrically connecting the components.

However, the FPCB may have a flexible characteristic different from a general circuit board (e.g., a PCB). Accordingly, the biometric sensor according to one embodiment disclosed in the present disclosure may include the FPCB so as to be configured to have a corresponding curve according to the shape of the body in contact with the biometric sensor.

In other words, the body may have a part having a high curvature and a part having a low curvature, and the curvatures may be different depending on the part of the body. Here, in order to obtain accurate biometric information, the shape of the biometric sensor needs to be configured to correspond to the shape of a region of the body, on which the sensor is used, which may be implemented using the FPCB having flexibility.

In addition, the biometric sensor according to one embodiment of the present disclosure may include a plurality of wires 51, 52, and 53 mounted in the FPCB 50.

The wires 51, 52, and 53 mounted in the FPCB 50 may connect an external electrical source to the light-emitting part 20, the light-receiving part 30, or the like to supply electrical energy to the light-emitting part 20, the light-receiving part 30, or the like. In the case of the light-emitting part 20, the electrical energy transmitted from the external electrical source through the wires 51 and 52 is converted into light energy and emitted as light energy of a specific wavelength by the light-emitting part 20. When a plurality of light-emitting parts are present, each of the plurality of light-emitting parts may be connected to the external electrical source through the wire.

In the case of the light-receiving part 30, light energy reflected by the object 110 inside the body 100 may be converted into electrical energy by the light-receiving part 30 through the wire 53. Here, changes in the object 110 inside the body 100 may be sensed on the basis of the intensity of the converted electrical energy.

For example, the converted electrical energy may be quantified as an indicator of the converted electrical energy, such as an intensity of current, and biometric information such as changes in blood vessels, blood flow, a heart rate, oxygen saturation, photoplethysmogram, photoplethysmography (PPG), and the like, or a combination thereof, may be measured through changes in the intensity of the current.

The biometric sensor according to one embodiment of the present disclosure may include the plurality of wires 51, 52, and 53 mounted in the FPCB. At this point, the wire may be formed in a small thickness (e.g., about 15 mm).

The plurality of wires 51 and 52 mounted in the FPCB 50 may be connected to the first and second light-emitting parts 21 and 22, respectively. Here, the wires may be connected to the first light-emitting part and the second light-emitting part through the elastomer or the flexible substrate.

The wires 51 and 52 may have a shape surrounded by the elastomer. When the wires 51 and 52 are placed in an unfixed state in a region between the FPCB 50 and the first light-emitting part 21 or the second light-emitting part 22 and then the elastomer 40 is applied to the flexible substrate 10 in a liquid or gel type, the elastomer 40 may be cured while the wires 51 and 52 are included in the elastomer 40.

Alternatively, the wires 51 and 52 may be located between the flexible substrate 10 and the elastomer 40. When the elastomer 40 is formed in a state in which the wires 51 and 52 are located on the flexible substrate 10, the wires 51 and 52 may be located between the flexible substrate 10 and the elastomer 40.

When connected through the elastomer, the wire may have a different configuration depending on the state (e.g., solid and liquid) at the time of manufacture of the elastomer.

For example, when the elastomer is manufactured in a liquid state, the wires 51 and 52 may be solidified in a shape surrounded by the elastomer in a liquid state, and finally, the wires may be surrounded by the elastomer. When the elastomer is manufactured in a solid state, the wires 51 and 52 may be disposed between the elastomer and the flexible substrate and connected to the first and second light-emitting parts.

According to one embodiment disclosed in the present disclosure, the biometric sensor may include at least one or more protective layers. The protective layer may perform a function of blocking air including moisture and/or oxygen outside the biometric sensor from flowing into the sensor. Alternatively, the protective layer may prevent various foreign substances (e.g. dust or the like) other than moisture and/or oxygen, which reduce the accuracy of the biometric sensor, from being introduced into the sensor.

According to one embodiment disclosed in the present disclosure, the biometric sensor may include at least one or more protective layers. In this case, one protective layer of at least one or more protective layers may be located on one side of the light-receiving part. Referring to FIG. 2, the protective layer 60 may be configured to surround an upper portion of the light-receiving part 30. Here, the light-receiving part 30 may be located on one side of the flexible substrate 10, and the light-receiving part 30 and the flexible substrate 10 may be formed to have different sizes. In this case, the protective layer 60 may be configured to shield side surface portions of the light-receiving part 30 and at least a portion of left and right side portions of an upper surface of the flexible substrate 10.

Although not shown in the drawings, the biometric sensor may include an additional protective layer in a part in contact with the body (e.g., a lower part of each of the FPCB, the light-emitting part, and the elastomer in FIG. 2). Thus, foreign substances of the body or moisture and/or oxygen present in the body may be prevented from flowing into the inside of the biometric sensor.

Here, the additional protective layer may be located on a moving path of light irradiated from the light-emitting part toward the body. Alternatively, the additional protective layer may be located on a path through which light reflected by the object inside the body moves toward the light-receiving part. In this case, the additional protective layer may be made of any suitable material so as not to absorb or interfere with light emitted from the light-emitting part and light reflected by the object in the body. The additional protective layer may be made of the same material as the protective layer 60. The additional protective layer may be integrally formed with the protective layer 60.

Hereinafter, the movement of light in the biometric sensor according to the embodiment will be described.

Figure 4:
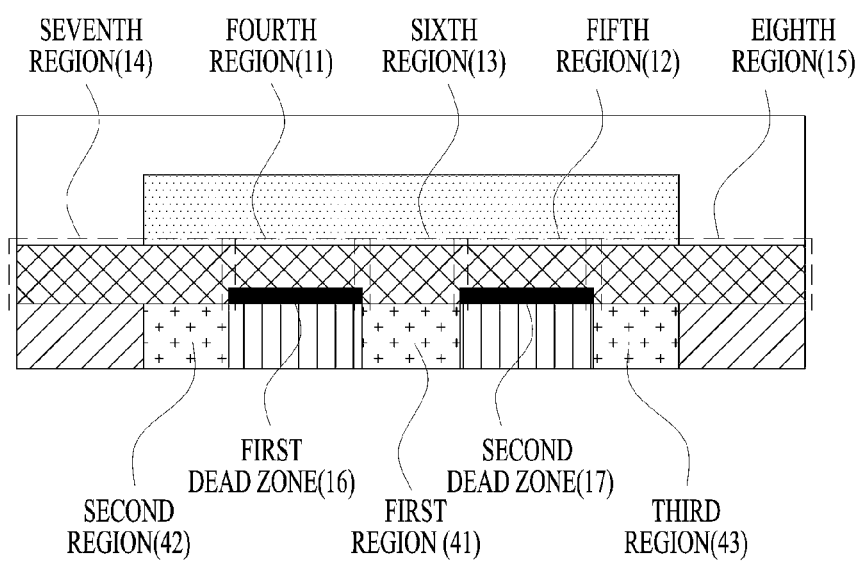
FIG. 4 is a cross-sectional view illustrating a plurality of regions of an elastomer and a flexible substrate in the biometric sensor according to one embodiment of the present application.

FIG. 4 is a cross-sectional view illustrating a plurality of regions of the elastomer and the flexible substrate in the biometric sensor according to one embodiment of the present application.

Descriptions of the locations of the regions, the relationship between the regions, the path of light output from the light-emitting part and entering the light-receiving part, and characteristics of light transmitted for each region will be provided.

Referring to FIGS. 2 and 4, the elastomer 40 may include a first region 41, a second region 42, and a third region 43.

The first region 41 may be a region located between one side of the first light-emitting part 21 and one side of the second light-emitting part 22.

The second region 42 may be a region located between the first light-emitting part 21 and the FPCB 50. Specifically, the second region 42 may be a region located on a side opposite to one side of the first light-emitting part 21, which is connected to the first region 41. In other words, the second region 42 may be a region located between the other side of the first light-emitting part 21 and the FPCB 50.

The third region 43 may be a region located between the second light-emitting part 22 and the FPCB 50. Specifically, the third region 43 may be a region located on a side opposite to one side of the second light-emitting part 22, which is connected to the first region 41. In other words, the third region 43 may be a region located between the other side of the second light-emitting part 22 and the FPCB 50.

The first region 41, the second region 42, and the third region 43 may be formed to have a height corresponding to the height of each of the first and second light-emitting parts 21 and 22 and the FPCB 50. Since the first region 41, the second region 42, and the third region 43 have the height corresponding to that of each of the first and second light-emitting parts 21 and 22 and the FPCB 50, all the components of the biometric sensor may be manufactured without a step difference.

Since all the components of the biometric sensor may be manufactured without a step difference, a separation between the body to be measured and the biometric sensor may be prevented for each region, thereby improving measurement accuracy.

In addition, the biometric sensor according to one embodiment of the present disclosure may include the flexible substrate 10 including a fourth region 11 having a first dead zone 16 in contact with the first light-emitting part 21 and a fifth region 12 having a second dead zone 17 in contact with the second light-emitting part 22. In the biometric sensor according to one embodiment of the present disclosure, the first and second light-emitting parts 21 and 22 may be disposed on the other side of the flexible substrate 10, and in this case, the first and second light-emitting parts are disposed on a lower layer with respect to the flexible substrate 10, and there may be a dead zone in which reflected light (e.g., third light and fourth light) originating from the first and second light-emitting parts does not reach the portion of the flexible substrate on which the first light-emitting part and the second light-emitting part are located. In other words, the flexible substrate may include the first dead zone 16 and the second dead zone 17 in which reflected light originating from the first light-emitting part and reflected light originating from the second light-emitting part are not transmitted.

However, the reflected light originating from the first light-emitting part and the reflected light originating from the second light-emitting part may be transmitted through a region included in the fourth region 11 other than the first dead zone 16. In addition, the reflected light originating from the first light-emitting part and the reflected light originating from the second light-emitting part may be transmitted through a region included in the fifth region 12 other than the second dead zone 17.

Further, the flexible substrate 10 of the biometric sensor according to one embodiment of the present disclosure may include a sixth region 13, a seventh region 14, and an eighth region 15.

The sixth region 13 may be a region located between one side of the fourth region 11 of the flexible substrate and one side of the fifth region 12.

The seventh region 14 may be located on a side opposite to one side of the fourth region 11, which is connected to one side of the sixth region 13. In other words, the seventh region 14 may be a region in the flexible substrate located at the other side of the fourth region 11.

The eighth region 15 may be located on a side opposite to one side of the fifth region 12, which is connected to the other side of the sixth region 13. In other words, the eighth region 15 may be a region in the flexible substrate located at the other side of the fifth region 12.

The sixth region 13, the seventh region 14, and the eighth region 15 may be a transmission path of reflected light when light output from the light-emitting parts 21 and 22 is reflected by the object inside the body and is incident on the light-receiving part.

The first light output from the first light-emitting part 21 is reflected by the object 110 inside the body, sequentially transmitted through the elastomer 40 and the flexible substrate 10, and transmitted to and received by the light-receiving part 30 as the third light. At this point, the reflected light of the first light is transmitted through at least one of the first region 41, the second region 42, and the third region 43 of the elastomer 40. The reflected light of the first light transmitted through the elastomer 40 may be transmitted through at least one region of the sixth region 13, the seventh region 14, the eighth region 15, a partial region of the fourth region 11, and a partial region of the fifth region 12 of the flexible substrate 10 and may be incident on the light-receiving part 30 as the third light.

Similarly, the second light output from the second light-emitting part 22 is reflected by the object 110 inside the body, sequentially transmitted through the elastomer 40 and the flexible substrate 10, and transmitted to and received by the light-receiving part 30 as the fourth light. At this point, the reflected light of the second light is transmitted through at least one of the first region 41, the second region 42, and the third region 43 of the elastomer 40. The reflected light of the second light transmitted through the elastomer 40 may be transmitted through at least one region of the sixth region 13, the seventh region 14, the eighth region 15, a partial region of the fourth region 11, and a partial region of the fifth region 12 of the flexible substrate 10 and may be incident on the light-receiving part 30 as the fourth light.

At this point, the transmitted amount of the third light may be greater in the first region 41 of the elastomer 40 than in the third region 43 of the elastomer 40. This is due to the structural features in which the first and second light-emitting parts 21 and 22 are disposed at a predetermined interval, the light-receiving part 30 and the light-emitting part 20 including the first and second light-emitting parts 21 and 22 are not disposed on the same layer, and the light-receiving part 30 is stacked on an upper layer of the light-emitting part 20.

Further, due to such structural features, when the third light is transmitted through the flexible substrate 10 and incident on the light-receiving part 30, the transmitted amount of the third light may be greater in the sixth region of the flexible substrate 10 than in the eighth region 15 of the flexible substrate 10.

Similarly, the second light output from the second light-emitting part 22 may be reflected by the object 110 inside the body, transmitted through at least one of the first region 41, the second region 42, and the third region 43 of the elastomer 40, and transmitted to and received by the light-receiving part 30 as the fourth light. At this time, the transmitted amount of the fourth light may be greater in the first region 41 of the elastomer 40 than in the second region 42 of the elastomer 40.

In addition, when the fourth light is transmitted through the flexible substrate 10 and incident on the light-receiving part 30, the transmitted amount of the fourth light may be greater in the sixth region 13 of the flexible substrate 10 than in the seventh region 14 of the flexible substrate 10.

The first light-emitting part and the second light-emitting part of the biometric sensor according to one embodiment of the present application may be driven in a time-division manner.

Hereinafter, the biometric sensor driven in the time-division manner will be described.

Figure 5:
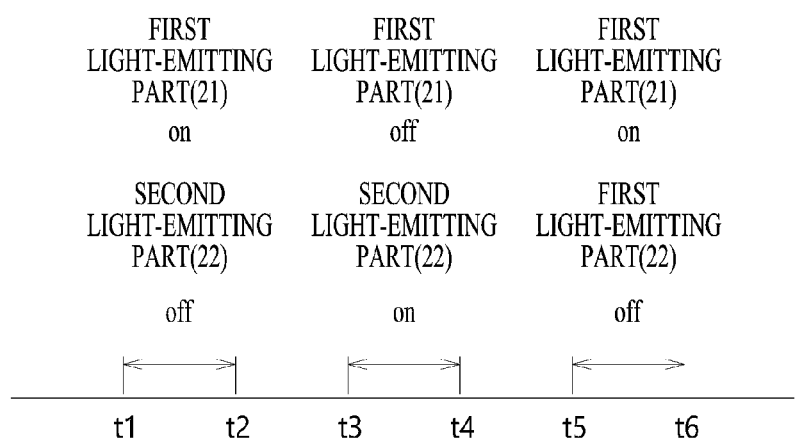
FIG. 5 is a view illustrating a timeline in which a first light-emitting part and a second light-emitting part of the biometric sensor according to one embodiment of the present application are operated to alternately output light.
Figure 6:
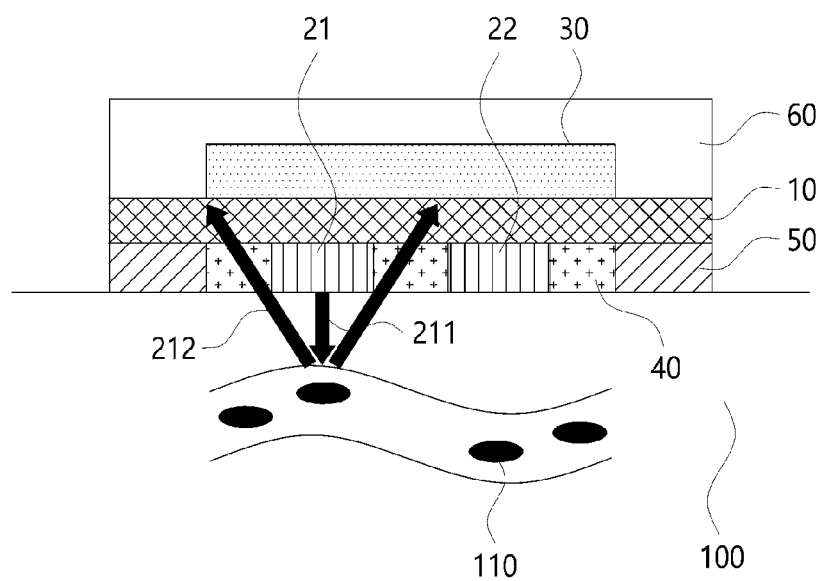
FIG. 6 is a cross-sectional view illustrating output light and reflected light in a case in which the first light-emitting part of the biometric sensor according to one embodiment of the present application is operated to output light.
Figure 7:
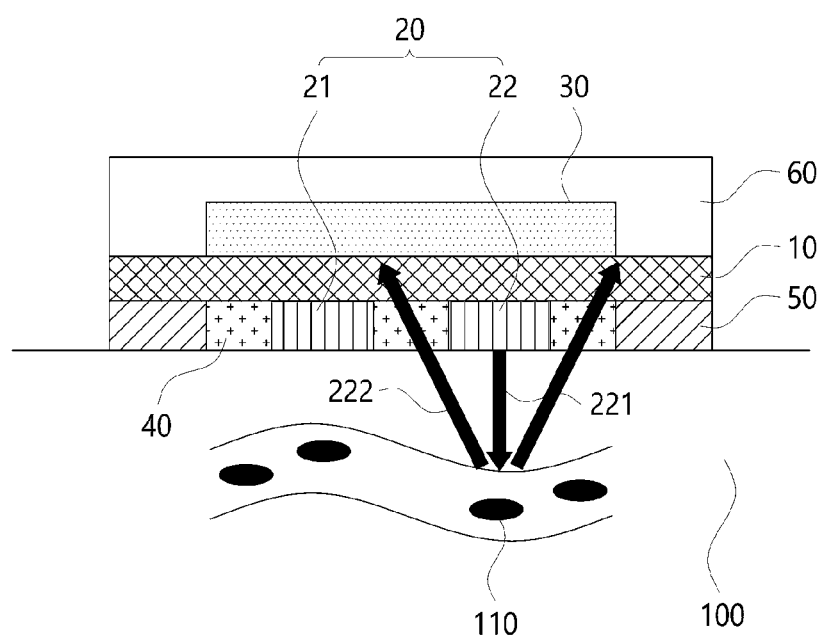
FIG. 7 is a cross-sectional view illustrating output light and reflected light in a case in which the second light-emitting part of the biometric sensor according to one embodiment of the present application is operated to output light.

FIG. 5 is a view illustrating a timeline in which the first light-emitting part and the second light-emitting part of the biometric sensor according to one embodiment of the present application are operated to alternately output. FIG. 6 is a cross-sectional view illustrating output light and reflected light in a case in which the first light-emitting part of the biometric sensor according to one embodiment of the present application is operated to output light. FIG. 7 is a cross-sectional view illustrating output light and reflected light in a case in which the second light-emitting part of the biometric sensor according to one embodiment of the present application is operated to output light. FIGS. 8A and 8B are graphs respectively illustrating output currents generated by receiving and converting each of the reflected light in FIGS. 6 and 7 by the light-receiving part.

Referring to FIG. 5, the first light output from the first light-emitting part may be output for a first period, and the second light output from the second light-emitting part may be output for a second period. For example, the first light-emitting part 21 is operated to output the first light in a period t1 to t2 (or a period t5 to T6), and the second light-emitting part 22 is operated in a period t3 to t4 to output the second light.

In this case, the first light and the second light may be alternately output. In other words, in the period t1 to t2 (or the period t5 to t6), it is controlled so that only the first light-emitting part 21 is operated and the second light-emitting part 22 is not operated so that only the first light is output. In addition, in the period t3 to t4, it is controlled so that only the second light-emitting part 22 is operated and the first light-emitting part 21 is not operated to output only the second light. An interference problem between the first light and the second light may be solved by alternately outputting the first light and the second light. The controller may control the first light-emitting part 21 and the second light-emitting part 22 so that the first light and the second light are alternately output.

Further, the biometric sensor according to one embodiment of the present disclosure may include the controller. The controller may be configured to detect first information related to the biometric information on the basis of the third light that is reflected light of the first light and incident on the light-receiving part. Similarly, the controller may be configured to detect second information related to the biometric information on the basis of the fourth light that is reflected light of the second light and incident on the light-receiving part.

For example, when only the first light-emitting part 21 is operated for the period t1 to t2 (or the period t5 to t6) to output the first light toward the body, the third light, which is the first light reflected by the inside of the body and incident on the light-receiving part, is received by the light-receiving part for a period corresponding to the period t1 to t2 (or the period t5 to t6), and the first information related to the biometric information (e.g., blood vessel movement, heart rate, or the like) may be detected on the basis of the third light.

In addition, when only the second light-emitting part 22 is operated for the period t3 to t4 to output the second light toward the body, the fourth light, which is the second light reflected by the inside of the body and incident on the light-receiving part, is received by the light-receiving part for a period corresponding to the period t3 to t4, and second information related to biometric information (e.g., blood vessel movement, heart rate, or the like) may be detected on the basis of the fourth light.

Reference is made to FIG. 6. FIG. 6 is a cross-sectional view illustrating output light and reflected light in a case in which the first light-emitting part of the biometric sensor according to one embodiment of the present application is operated to output light. Since the first and second light-emitting parts 21 and 22 may alternately output light, FIG. 6 may be a view illustrating a state in which the second light is not output from the second light-emitting part and first light 211 is output only from the first light-emitting part 21.

Referring to FIG. 6, the first light 211 is output from the first light-emitting part 21 toward the body 100 located in a region in a direction opposite to a direction in which the flexible substrate 10 is located. The first light 211 may be reflected by the object 110 located inside the body 100, and transmitted through the elastomer 40 and the flexible substrate 10, and received by the light-receiving part 30 as third light 212. At this point, the third light 212 may refer to light at a time point at which the light is reflected by the object inside the body, or may refer to light at a time point at which the light is received by the light-receiving part.

Thereafter, the controller may detect the first information for heart rate and oxygen saturation on the basis of the third light received by the light-receiving part 30.

Reference is made to FIG. 7. FIG. 7 is a cross-sectional view illustrating output light and reflected light in a case in which the second light-emitting part of the biometric sensor according to one embodiment of the present application is operated to output light. Since the first and second light-emitting parts 21 and 22 may alternately output light, FIG. 7 may be a view illustrating a state in which the first light is not output from the first light-emitting part and second light 221 is output only from the second light-emitting part 22.

Referring to FIG. 7 again, the second light 221 is output from the second light-emitting part 22 toward the body 100 located in a region in a direction opposite to a direction in which the flexible substrate 10 is located. The second light 221 may be reflected by the object 110 located inside the body 100, and transmitted through the elastomer 40 and the flexible substrate 10 and received by the light-receiving part 30 as fourth light 222. At this point, the fourth light 222 may refer to light at a time point at which the light is reflected by the object inside the body, or may refer to light at a time point at which the light is received by the light-receiving part.

Thereafter, the controller may detect the second information for heart rate and oxygen saturation on the basis of the fourth light received by the light-receiving part 30.

Figure 8:
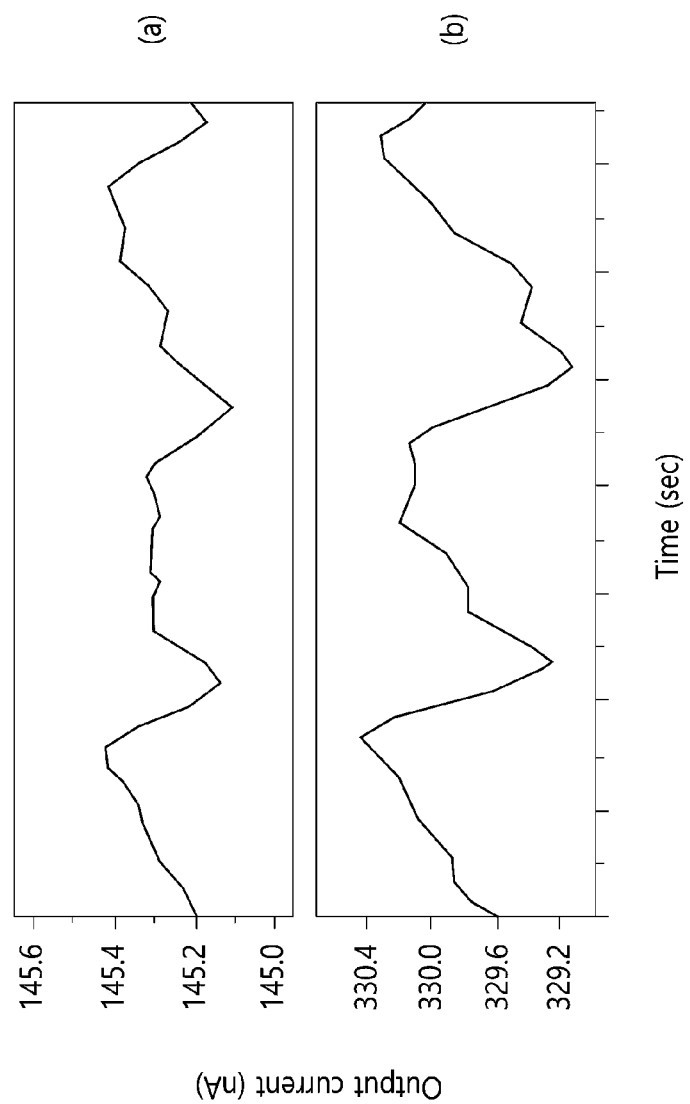
FIG. 8 shows graphs respectively illustrating output currents generated by receiving and converting the reflected light in FIGS. 6 and 7 by a light-receiving part.

Reference is made to FIG. 8. FIGS. 8A and 8B are graphs respectively illustrating output currents generated by receiving and converting each of the reflected light in FIGS. 6 and 7 by the light-receiving part. FIG. 8A illustrates an output current, which is converted from the third light by the light-receiving part 30 after receiving the third light, which is reflected light corresponding to the first light, in the case in which only the first light is output from the first light-emitting part 21 of FIG. 6. For example, when the first light-emitting part 21 is a red LED and the first light 211 is output toward the body for the period t1 to t2 (or the period t5 to t6), the third light 212 reflected by the object of the body is received by the light-receiving part 30 through the elastomer 40 and the flexible substrate 10, and the received light energy is converted into and output as a current.

Similarly, FIG. 8B illustrates an output current, which is converted from the fourth light by the light-receiving part 30 after receiving the fourth light, which is reflected light corresponding to the second light, in the case in which only the second light is output from the second light-emitting part 22 of FIG. 7. For example, when the second light-emitting part 22 is an NIR LED and the second light 221 is output toward the body for the period t3 to t4, the fourth light 222 reflected by the object of the body is received by the light-receiving part 30 through the elastomer 40 and the flexible substrate 10, and the received light energy is converted into and output as a current.

In addition, the biometric sensor according to one embodiment of the present disclosure may include the controller. The controller may be configured to sense changes in blood vessels, blood flow, a heart rate, oxygen saturation, photoplethysmogram, photoplethysmography (PPG), or a combination thereof using the first information detected on the basis of the third light and the second information detected on the basis of the fourth light.

For example, the movement of the blood vessel may be measured using the converted output current value of each light received by the light-receiving part. Specifically, when light (photons) emitted from the light-emitting part is incident into the body, the light may be scattered through various scattering media inside the body. The scattered light may be scattered in all directions inside the body, and some of the light may further penetrate into the body or be absorbed into the body. In addition, the light may be reflected or back-scattered in an incident direction, and the reflected light may be transmitted to the light-receiving part. At this point, there may be a part that is not moving in the body and a part whose light absorption level is changed according to the movement of blood vessels inside the body. A strength or intensity of the reflected light may be different depending on whether the light is reflected by the part that is not moving in the body or the part whose light absorption level is changed according to the movement of blood vessels inside the body, and the strength of the reflected light may be received by the light-receiving part and converted into electrical energy (e.g., current value).

At this time, since the current value may be output differently according to the part of the inside of the body, the movement of the blood vessels may be extracted from changes in current value or changes in voltage value of an external receiving circuit connected to the light-receiving part.

Further, the oxygen saturation may be measured using the converted output current value of each reflected light received by the light-receiving part. Saturated hemoglobin and unsaturated hemoglobin inside the body have different molar extinction coefficients for specific light energy, and the oxygen saturation may be extracted using two signals output from the light-receiving part by emitting light of two different wavelengths toward the body.

The biometric sensor according to one embodiment of the present disclosure may efficiently receive light through the structure and shape in which the flexible substrate, the light-receiving part, and the light-emitting part are disposed, and by using the flexible substrate, the light-receiving part, the elastomer, and the FPCB, the shape of the biometric sensor may be implemented so that the biometric sensor is brought into close contact with the body.

In addition, the biometric sensor according to one embodiment of the present disclosure has high light reception efficiency and thus may be driven with ultra-low power.

Further, unlike the conventional oxygen saturation detection sensor in which a light-emitting part is configured as an OLED, by configuring a light-emitting part as an LED, an oxygen saturation detection sensor that requires high brightness may receive light more efficiently, and an oxygen saturation detection sensor that may achieve high performance may be implemented.

Further, when a red LED and an NIR LED are used as a light-emitting part, there are advantages in that the biometric sensor may be implemented in a reflection method rather than a transmission method and implemented more efficiently in terms of power when the biometric sensor is driven in the reflection method than when the biometric sensor is driven in the transmission method.

Using the above-described advantages, the biometric sensor according to one embodiment of the present disclosure is applicable to a clamp-type heart rate and oxygen saturation sensor used for medical purposes. In this case, the clamp-type heart rate and oxygen saturation sensor may be implemented by disposing the biometric sensor according to one embodiment of the present disclosure only on one surface of the clamp, which is in contact with a body.

Further, the biometric sensor according to one embodiment of the present disclosure is applicable to a heart rate sensor used by being embedded in a wearable device such as a watch, a smartphone, and an earphone Since the biometric sensor according to one embodiment of the present disclosure may be manufactured in a small size and driven with ultra-low power, there are various types of wearable devices to which the biometric sensor is applicable, such as watches, smartphones, earphones, underwear, glasses, and bracelets.

In addition, the biometric sensor according to one embodiment of the present disclosure may be used to monitor and sense biometric information of an elderly or severely ill patient required to be observed all times through biometric monitoring. The biometric sensor that may be driven with ultra-low power is also applicable to a disposable patch-type healthcare sensor.

The biometric sensor is not limited thereto, and is applicable to all sensors for sensing biometric information including heart rate and oxygen saturation.

According to an embodiment of the present disclosure, a biometric sensor can remarkably increase light receiving efficiency.

Accordingly, a low-power-based biometric sensor can be implemented.

Further, a biometric sensor has high external quantum efficiency at high brightness, and thus can be easily applied to a heart rate and oxygen saturation sensor.

Further, a biometric sensor is flexible and has a high degree of freedom in pattern formation by using organic semiconductor elements and thus can be implemented in various forms.

In addition, a biometric sensor can be attached by being in close contact with a body according to the shape of the body, and thus it is easy to measure a stable biometric signal and can be applied to various body parts.

It is to be understood that the effect of the present disclosure is not limited to the above-described effects and can be expanded in various ways without departing from the spirit and scope of the present disclosure.

The features, structures, effects, and the like described in the above embodiments are included in at least one embodiment of the present disclosure, but the present disclosure is not necessarily limited to only one embodiment. Furthermore, the features, structures, effects, and the like illustrated in the embodiments may be combined and modified in other embodiments by those skilled in the art. Therefore, it should be interpreted that contents related to the combinations and modifications are included in the present disclosure.

In addition, while the present disclosure has been mainly described above with reference to the embodiments, it should be understood by those skilled in the art that the disclosure is not limited to the embodiments, but the embodiments are only examples, and various modifications and applications which are not illustrated above may fall within the range of the present disclosure without departing from the essential features of the present embodiments.

That is, components specifically described in the embodiments may be modified and implemented.

In addition, it should be understood that differences related to modifications and applications fall within the scope of the present disclosure defined by the appended claims.

What is claimed is:

1. A biometric sensor for sensing biometric information of a body, the biometric sensor comprising:
a flexible substrate;
a first emitter configured to output a first light towards the body, wherein the first emitter is disposed on a first side of the flexible substrate;
a second emitter configured to output a second light different from the first light towards the body, wherein the second emitter is disposed on the first side of the flexible substrate and spaced apart from the first emitter;
an elastomer configured to have a height corresponding to a height of the first emitter and a height of the second emitter, wherein the elastomer is disposed on the first side of the flexible substrate; and
a receiver configured to receive a third light corresponding to the first light and a fourth light corresponding to the second light, wherein the receiver is disposed on a second side of the flexible substrate, wherein the second side of the flexible substrate is opposite to the first side of the flexible substrate, and wherein the third light is at least a portion of reflected light of the first light at the body and the fourth light is at least a portion of reflected light of the second light at the body;
wherein the elastomer includes a first region disposed between the first emitter and the second emitter, and
wherein the receiver is configured to receive the third light and the fourth light when transmitted sequentially through the first region of the elastomer and the flexible substrate.

2. The biometric sensor of claim 1, wherein a wavelength of the first light output from the first emitter is different from a wavelength of the second light output from the second emitter.

3. The biometric sensor of claim 1, further comprising:
a controller configured to control the biometric sensor;
wherein
the first light output from the first emitter is output for a first period, the second light output from the second emitter is output for a second period, and
the first light and the second light are alternately output, and wherein
the controller detects first information on the basis of the third light incident on the receiver for the first period and detects second information on the basis of the fourth light incident on the receiver for the second period.

4. The biometric sensor of claim 1, wherein
the receiver is formed in a shape surrounding an upper surface of the first emitter and the second emitter, and
at least a partial surface of the receiver corresponding to a direction perpendicular to the upper surface of at least one of the first emitter and the second emitter and overlaps the upper surface of at least one of the first emitter and the second emitter.

5. The biometric sensor of claim 1, wherein
the receiver includes a first receiver and a second receiver,
the third light reflected by the body is received by at least one of the first receiver and the second receiver, and
the fourth light reflected by the body is received by at least one of the first receiver and the second receiver.

6. The biometric sensor of claim 1, wherein
the first light is output from the first emitter towards the body located in a region in a direction opposite to a direction in which the flexible substrate is located, and
the second light is output from the second emitter towards the body located in a region in the direction opposite to the direction in which the flexible substrate is located.

7. The biometric sensor of claim 1, wherein
the first emitter is a red light-emitting diode (red LED), and
the second emitter is a near infrared (NIR) LED.

8. The biometric sensor of claim 1, wherein the flexible substrate is made of polyethylene terephthalate (PET) through which the third light and the fourth light are transmitted.

9. The biometric sensor of claim 1, wherein
the elastomer is made of polydimethylsiloxane (PDMS), silicone, or a combination thereof through which the third light and the fourth light are transmitted.

10. The biometric sensor of claim 1, further comprising at least one or more protective layers configured to block external moisture and/or oxygen.

11. The biometric sensor of claim 1, wherein the elastomer further includes a second region and a third region,
wherein the second region is located at a side surface opposite to one side surface of the first emitter, which is connected to the first region,
the third region is located at a side surface opposite to one side surface of the second emitter, which is connected to the first region,
the second region or the third region is a path through which the third light and the fourth light reflected by the body are transmitted,
a transmitted amount of the third light corresponding to the first light emitted from the first emitter is greater in the first region than in the third region, and
a transmitted amount of the fourth light corresponding to the second light emitted from the second emitter is greater in the first region than in the second region.

12. The biometric sensor of claim 1, wherein
the flexible substrate includes a fourth region including a first dead zone in contact with the first emitter, a fifth region including a second dead zone in contact with the second emitter, and a sixth region disposed between the fourth region and the fifth region,
wherein the sixth region is a path through which the third light and the fourth light reflected by the body are transmitted, and
the first dead zone and the second dead zone do not transmit the third light and the fourth light.

13. The biometric sensor of claim 1, further comprising a flexible printed circuit board (FPCB) located on the first side of the flexible substrate,
wherein wires connected from an external power source are mounted in the FPCB.

14. The biometric sensor of claim 3, wherein the controller senses a change in blood vessels, blood flow, a heart rate, oxygen saturation, photoplethysmogram, photoplethysmography (PPG), or a combination thereof on the basis of the first information and the second information.

15. The biometric sensor of claim 11, wherein a size of the elastomer is set such that both the third light and the fourth light incident on the receiver are transmitted through the elastomer.

16. The biometric sensor of claim 12, wherein the flexible substrate further includes a seventh region and an eighth region, wherein the seventh region is located at a side opposite to one side of the fourth region, which is connected to one side of the sixth region, the eighth region is located at a side opposite to one side of the fifth region, which is connected to the other side of the sixth region, a transmitted amount of the third light corresponding to the first light emitted from the first emitter is greater in the sixth region than in the eighth region, and a transmitted amount of the fourth light corresponding to the second light emitted from the second emitter is greater in the sixth region than in the seventh region.

17. The biometric sensor of claim 13, wherein the first emitter and the second emitter are connected to the wires mounted in the FPCB, and the wires are configured to be surrounded by the elastomer or to be disposed between the flexible substrate and the elastomer.

18. The biometric sensor of claim 17, wherein the wires include a first wire and a second wire, the first wire is connected to the first emitter, and the second wire is connected to the second emitter.

* * * * *